United States Patent
Raman et al.

(10) Patent No.: US 12,134,795 B2
(45) Date of Patent: Nov. 5, 2024

(54) SENSOR FOR CYANURIC ACID DETECTION

(71) Applicant: WISCONSIN ALUMNI RESEARCH FOUNDATION, Madison, WI (US)

(72) Inventors: Srivatsan Raman, Middleton, WI (US); Xiangyang Liu, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1324 days.

(21) Appl. No.: 16/750,465

(22) Filed: Jan. 23, 2020

(65) Prior Publication Data

US 2020/0239927 A1 Jul. 30, 2020

Related U.S. Application Data

(60) Provisional application No. 62/798,128, filed on Jan. 29, 2019.

(51) Int. Cl.
| | |
|---|---|
| *C12N 15/62* | (2006.01) |
| *C12N 1/20* | (2006.01) |
| *C12N 15/113* | (2010.01) |
| *C12Q 1/02* | (2006.01) |
| *G01N 33/02* | (2006.01) |
| *G01N 33/18* | (2006.01) |
| *C07D 251/32* | (2006.01) |

(52) U.S. Cl.
CPC ............... *C12Q 1/02* (2013.01); *C12N 1/20* (2013.01); *C12N 15/113* (2013.01); *G01N 33/02* (2013.01); *G01N 33/1826* (2013.01); *C07D 251/32* (2013.01)

(58) Field of Classification Search
None
See application file for complete search history.

(56) References Cited

U.S. PATENT DOCUMENTS

2019/0062730 A1   2/2019   Raman et al.

FOREIGN PATENT DOCUMENTS

EP        0348493 B1       1/1990

*Primary Examiner* — Michael D Pak
(74) *Attorney, Agent, or Firm* — Karen A. LeCuyer; DeWitt LLP

(57) ABSTRACT

A cyanuric acid-responsive biosensor includes a host strain or cell-free system including a first and a second expression cassette; the first expression cassette including, in operable communication, a constitutive promoter and a gene encoding an AtzR cyanuric acid-responsive transcription factor; and the second expression cassette including, in operable communication, a promoter regulated by the cyanuric acid-responsive transcription factor and a gene encoding a reporter protein, wherein the first expression cassette expresses the AtzR cyanuric acid-responsive transcription factor, and, in the presence of cyanuric acid, the AtzR cyanuric acid-responsive transcription factor drives expression of the reporter protein.

15 Claims, 10 Drawing Sheets
Specification includes a Sequence Listing.

SENSOR FOR CYANURIC ACID DETECTION

CROSS-REFERENCE TO RELATED APPLICATIONS

This application claims priority to U.S. Provisional Application 62/798,128 filed on Jan. 29, 2019, which is incorporated herein by reference in its entirety.

FIELD OF THE DISCLOSURE

The present disclosure is related to biosensors and methods for the detection of cyanuric acid.

BACKGROUND

Cyanuric acid belongs to a class of cyclic six-membered heterocyclic ring compounds made of alternating carbon and nitrogen known as triazines. Cyanuric acid is a high-volume industrial chemical produced by pyrolysis of urea. It is widely used as a swimming pool disinfectant, household bleach, industrial cleanser, dishwasher detergent, and general-purpose sanitizer. Chlorine is administered in swimming pools, spas, and fountains to prevent the growth of microbes and organic contaminants. However, when exposed to ultraviolet radiation from sunlight, chlorine disintegrates and loses efficacy quickly. Cyanuric acid is used in the manufacture of chlorine tablets because it forms a weak bond with free chlorine and acts as a slow-release agent that stabilizes chlorine and prevents rapid degradation. The concentration of cyanuric acid has to be carefully adjusted because too little is ineffective as a chlorine stabilizer, but excess cyanuric acid makes free chlorine less active in promoting the growth of algae and bacteria. Since cyanuric acid is rich in nitrogen, it also used as an adulterant to increase nitrogen content and consequently the apparent protein level in food. Although cyanuric acid by itself is non-toxic, cyanuric acid mixed with melamine, another common food adulterant, forms a crystalline adduct that may cause renal failure. Accumulation of this toxic substance in adulterated food was responsible for several deaths and led to the widespread recall of pet food and milk in 2007-08. Since cyanuric acid in the environment and in food impacts human health, there is a strong need for tools to detect and monitor cyanuric acid.

Current methods for detecting cyanuric acid fall into one of three categories: turbidometric, colorimetric or potentiometric methods. When a water sample containing cyanuric acid is mixed with melamine, it forms a finely dispersed precipitate whose turbidity is proportional to the concentration of cyanuric acid. Turbidity can be assessed visually or measured with an optical device to estimate the concentration of cyanuric acid. Cyanuric acid can be electrochemically sensed by mixing a sample containing cyanuric acid and copper sulfate with copper ions acting as charge carriers. The concentration of cyanuric acid affects the amount of free copper in solution which is proportional to the flow of current through the electrochemical circuit. Cyanuric acid can also be detected by colorimetric change of a pH-dependent dye because the acidity of the solution increases with increasing cyanuric acid. There are several drawbacks to current sensing methods. Electrochemical and colorimetric techniques do not measure cyanuric acid directly, instead they estimate the concentration of proxies such as copper ion and pH, respectively. Therefore, the measurement may be confounded by factors unrelated to cyanuric acid influencing these proxies. Furthermore, the test reagent has to be maintained within a narrow pH window to trigger a large pH-dependent color change and even small fluctuations in the pH of the test reagent can affect sensitivity and signal output. The cost of electrochemical sensing is higher because it requires a specially fabricated device to house the electrodes and reagent. Although turbidometry is a direct measurement of cyanuric acid, and is the most commonly used technique, it is highly unreliable due to subjective differences in visual assessment of turbidity.

What is needed are compositions and methods for the detection of cyanuric acid.

BRIEF SUMMARY

In one aspect a cyanuric acid-responsive biosensor comprises
  a host strain or cell-free system comprising a first and a second expression cassette,
  the first expression cassette comprising, in operable communication, a constitutive promoter and a gene encoding an AtzR cyanuric acid-responsive transcription factor, and
  the second expression cassette comprising, in operable communication, a promoter regulated by the cyanuric acid-responsive transcription factor and a gene encoding a reporter protein,
  wherein the first expression cassette expresses the AtzR cyanuric acid-responsive transcription factor, and, in the presence of cyanuric acid, the AtzR cyanuric acid-responsive transcription factor drives expression of the reporter protein.

In another aspect, a liquid-based assay, a paper strip, or a multi-well plate assay comprises the cyanuric acid-based biosensor.

In a still further aspect, a method of detecting cyanuric acid comprises contacting a sample suspected of containing cyanuric acid with the cyanuric acid-responsive biosensor described herein.

Figure 1:
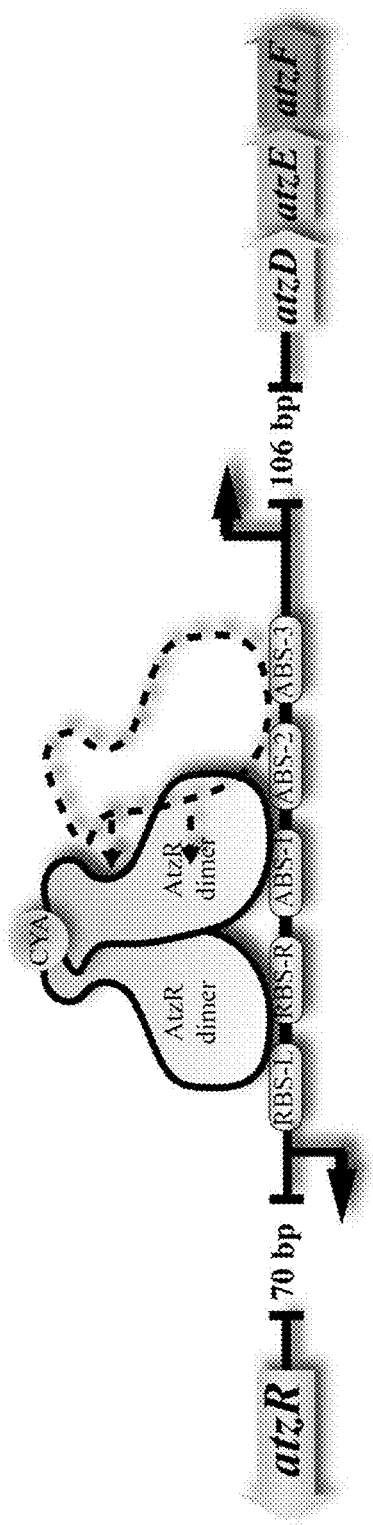
FIG. 1 shows the intragenic region between the atrazine regulator AtzR and its operator AtzDEF in *Pseudomonas* sp. AtzR binds to the operator sites (ABS and RBS) as a dimer of dimers. Each AtzR dimer is shown as a single blue drop-like shape. When cyanuric acid (pink dots) binds to AtzR, it causes one of the dimers to shift from binding ABS 2 and 3 to ABS 1 and 2.

The above-described and other features will be appreciated and understood by those skilled in the art from the following detailed description, drawings, and appended claims.

DETAILED DESCRIPTION

Described herein is a biological sensor for cyanuric acid. Biological sensors are a powerful alternative to current abiotic sensing approaches because of their specificity, sensitivity, and tunability. Transcription factors (TF) are widely used as biosensors in synthetic biology to detect small molecules. The concentration of small molecules can be measured in terms of a reporter gene expression in a dose-dependent manner. TF biosensors are autonomous, self-powered, miniaturizable, and programmable devices that function in both in vivo and ex vivo environments. TFs are allosterically activated upon binding to a small molecule whose concentration can be quantified by a transcriptionally-linked reporter gene.

In an aspect, the biosensor is a whole cell biological sensor. Bacterial whole cell biosensing is a powerful tool for monitoring pollutants, endocrine disruptors, trace elements and other toxins or contaminants affecting human and environmental health. Compared to purified proteins as biosensors, whole cells are cheaper, easier to manipulate and more stable under harsh environmental conditions. Whole cell biosensors take advantage of the innate capacity of bacteria to sense and respond to environmental cues and stressors. The goal of a whole cell biosensor is to express a protein (usually a reporter) by activating a cellular regulatory circuit. Since bacteria carry regulatory proteins to sense a multitude of molecules, the possibilities for building whole cell biosensors are seemingly endless. But, native regulatory circuits can be notoriously complicated with layered regulation making engineering difficult. This limits programmability of desirable biosensor properties including signal baseline, gain, reporter yield and sensitivity. Non-model host such as *Pseudomonas, Acinetobacter* and *Ralstonia* often contain biosensor circuits for many useful molecules.

The transcription regulator responding to a desired molecule can be ported from a non-model host into *E. coli*, for example. There are two advantages to this approach: (1) many standardized transcription/translation parts are available for circuit optimization (2) cell-free technologies for sensing toxic or cell-impermeable molecules is most advanced in *E. coli*. Bacterial transcription regulators employ various mechanisms for transcriptional control ranging from a simple repressor blocking RNA polymerase to complex regulation involving multi-protein interactions and structural deformation of DNA. Porting biosensor circuits with complex transcription into *E. coli* offers rich rewards by vastly expanding the repertoire of molecules detectable by an *E. coli*-based whole cell or cell-free biosensor. Cell-free technologies provide capabilities that could augment or supersede whole cell biosensing. Cell-free biosensing is particularly advantageous for analytes that are either toxic to the cell or difficult to transport across membrane boundaries. Because the native transcription machinery is weak in a cell-free environment, cell-free systems largely rely on a strong T7 RNA polymerase. However, new optimization techniques to increase the efficiency of native transcription, such as those described in U.S. Publication No. 2019/0062730 to Raman et al., has opened the possibilities of activating non-*E. coli* transcription regulators in an *E. coli* cell-free system.

Described herein is a whole-cell and a cell-free biosensor for cyanuric acid by engineering a biosensor circuit in *E. coli* using AtzR, a cyanuric acid-responsive LysR-type transcription regulator (LTTR) natively found in *Pseudomonas* sp. strain ADP1. *Pseudomonas* sp. ADP uses cyanuric acid as a nitrogen source by catabolizing the herbicide, atrazine. The atrazine regulator (AtzR) is a cyanuric acid-responsive TF that regulates a divergent operon (atzR-DEF) expressing the regulator (AtzR) itself and the enzymes (AtzD, AtzE and AtzF) involved in the uptake and conversion of cyanuric acid (FIG. 1). *E. coli* is a superior chassis for biosensing over *Pseudomonas* because unlike *E. coli*, *Pseudomonas* lacks well-characterized, modular transcription-translation parts and cell-free technologies for biosensing applications. However, it was shown that PatzR-DEF divergent promoters could not be activated in *E. coli* by AtzR and cyanuric acid. Although AtzR is a promising candidate for a TF biosensor, the mechanism of AtzR is complex and the native *Pseudomonas* promoter is not easily tunable due to layered regulation. The promoter for AtzR gene (PatzR) is controlled by $\sigma^{54}$, a conditionally-activated alternative σ-factor which is far less abundant and transcriptionally weaker than housekeeping $\sigma^{70}$, and is also co-regulated by a nitrogen-sensing TF, NtrC. PatzDEF is driven by *Pseudomonas* $\sigma^{70}$ and is also subject to general nitrogen regulator, GlnK, via protein-protein interactions. The 5' UTRs of PatzDEF (>100 bp) and PatzR (>70 bp) are unannotated sequences that may harbor additional cryptic sites (FIG. 1). Thus, to repurpose AtzR as a cyanuric acid biosensor, the inventors reengineered the promoter for compatibility to *E. coli* by carefully removing regulatory elements without disrupting the overall architecture required for transcription.

Specifically, described herein is a biosensor for cyanuric acid designed by reengineering the native atzR-DEF promoter from *Pseudomonas* ADP1 into *E. coli*. To adapt the PatzDEF for *E. coli*, the inventors replaced portions of the native *Pseudomonas* promoter with elements of a strong, synthetic *E. coli* promoter, while retaining the overall architecture of the native promoter. The auto-regulated, $\sigma^{54}$-dependent expression of AtzR was replaced with AtzR independently expressed from a well-characterized constitutive *E. coli* promoter and ribosome binding site (RBS). Out of the 16 promoter variants built and tested, 13 (SEQ ID:

3, 4, 7, 8, 9, 10, 12, 13, 14, 15, 16, 17 and 18) were transcriptionally more active than WT promoter in *E. coli* as measured by reporter expression. 6 (SEQ ID: 4, 7, 8, 10, 12 and 15) out of the 13 gave greater than two-fold increase in reporter expression in response to cyanuric acid. The best performing promoter variants gave 12-fold and 5-fold increases in reporter expression when induced with cyanuric acid (200 μM) in minimal and rich media, respectively. To evaluate the utility of the cyanuric acid biosensor for field applications, the limit of detection was assessed for a simple visual readout and the time-response for reporter signal. The biosensor gave a lower limit of detection at 5 μM (approximately 0.6 ppm) and 15 μM (approximately 2 ppm) in rich and minimal media, respectively, and an upper limit at 750 μM (approximately 94 ppm) in both media. Thus, the dynamic range of the biosensor encompasses cyanuric acid concentrations normally found in swimming pools (around 50 ppm). The time of response for visual detection was determined over background across a range of cell densities and it was determined that the fastest response time was two hours at an optical density of 2-8.

In an embodiment, a cyanuric acid-responsive biosensor comprises
a host strain or cell-free system comprising a first and a second expression cassette,
the first expression cassette comprising, in operable communication, a constitutive promoter and a gene encoding an AtzR cyanuric acid-responsive transcription factor, and
the second expression cassette comprising, in operable communication, a promoter regulated by the cyanuric acid-responsive transcription factor and a gene encoding a reporter protein,
wherein the first expression cassette expresses the AtzR cyanuric acid-responsive transcription factor, and, in the presence of cyanuric acid, the AtzR cyanuric acid-responsive transcription factor drives expression of the reporter protein.

In operable communication means that the nucleotide sequence of interest is linked to the regulatory sequence(s) in a manner that allows for expression of the transcription factor or the reporter gene, for example. The expression cassettes can be operably linked in any location, or multiplicity, so long as they are operably linked to allow for expression of the operably linked gene. Exemplary reporter proteins include GFP and FbFP (anaerobic condition).

The first expression cassette and the second expression cassette may be on the same or different DNA molecules, such as the same or different plasmids or chromosomes. In a specific aspect, the first expression cassette is present in a high or low copy number sensor plasmid, and the second expression cassette is present on a reporter plasmid. In certain embodiments, the cyanuric acid-responsive transcription factor is AtzR, the constitutive promoter comprises SEQ ID NO: 21, and the promoters regulated by the cyanuric acid-responsive transcription factors preferably have SEQ ID NOS: 3, 4, 7, 8 or 10.

Exemplary host strains can include both prokaryotes and eukaryotes. In an embodiment, the host strain comprises organisms of the genus *Escherichia, Bacillus, Staphylococcus, Caulobacter, Streptococcus, Streptomyces, Mycoplasma, Aliivibrio, Synechocystis, Azotobacter, Pseudomonas, Agrobacterium, Zymomonas, Saccharomyces, Yarrowia, Pichia* or a combination comprising at least one of the foregoing. Host strains and examples are provided in Table 1:

TABLE 1

| Organism genera and example species | | |
|---|---|---|
| System | Organism genus | Example species |
| Prokaryotes | Escherichia | E. coli |
|  | Bacillus | B. subtilis, B. thermophiles, B. anthracis |
|  | Staphylococcus | S. aureus, S. epidermidis |
|  | Caulobacter | C. Crescentus |
|  | Streptococcus | S. pyogenes, S. pneumoniae |
|  | Thermus | T. aquaticus, T. thermophilus |
|  | Streptomyces | S. coelicolor, S. antibioticus, S. avermitilis |
|  | Mycoplasma | M. Pneumoniae, M. genitalium |
|  | Aliivibrio | A. fischeri |
|  | Synechocystis | S. sp PCC6803 |
|  | Azotobacter | A. vinelandii |
|  | Pseudomonas | P. aeruginosa, P. putida, P. syringae |
|  | Agrobacterium | A. tumefaciens |
|  | Zymomonas | Z. mobilis |
| Eukaryotes | Saccharomyces | S. cerevisiae |
|  | Yarrowia | Y. lipolytica |
|  | Pichia | P. pastoris |

A specific host strain is *E. coli*, which can be grown in rich or minimal media. When the host strain is *E. coli*, the device can have a detection time of about 2 hours at an optical density of 2-8.

The cyanuric acid-responsive biomarkers described herein can have a lower detection limit of about 5 μM (or about 0.6 PPM) cyanuric acid, and an upper detection limit of about 750 μM (or about 94 PPM).

Exemplary reporter proteins include GFP and FbFP.

Also included herein are liquid-based assays, paper strips, or multi-well plate assays (96 well or 384 well plates, for example) comprising the cyanuric acid-based biosensors described herein.

A method of detecting cyanuric acid comprises contacting a sample suspected of containing cyanuric acid with the cyanuric acid-responsive biosensors described herein. Exemplary samples include food samples, including pet food samples. Cyanuric acid is used as a food additive to increase protein levels in processed food and animal food. Cyanuric acid combined with melamine is nephrotoxic, and has been identified as the source of toxicity in the pet food recalls.

In another aspect, the sample is a cleansing composition (e.g., household and industrial cleaners such as dishwasher detergents and multipurpose cleansers), a sanitizing composition (i.e., household and industrial disinfectants), or an herbicidal composition. Cyanuric acid is used as a precursor for such compositions.

In another aspect, the sample is a water sample, such as from a body of water such as a lake, a pool, a spa or a fountain. The cyanuric acid-responsive biosensors may be combined in a pool test kit with reagents suitable for the detection of pH, chlorine levels, bromine levels, water hardness, acid demand, total alkalinity, or a combination thereof.

Also included is a pool test kit comprising the cyanuric acid-responsive biosensor as described herein and a reagent suitable for the detection of pH, chlorine levels, bromine levels, water hardness, acid demand, total alkalinity, or a combination thereof. Reagents suitable for the detection of pH, chlorine levels, bromine levels, water hardness, acid demand, and total alkalinity are well-known in the art.

The invention is further illustrated by the following non-limiting examples.

EXAMPLES

Methods

Cloning and plasmids: Sensor plasmids were constructed on a plasmid backbone carrying a Spectinomycin-resistant gene. Two sensor plasmids carrying SC101 origins of replication were made, a high and a low copy plasmid. The high copy plasmid has the high copy version of SC101, while the other one has the low copy version of SC101. Both sensor plasmids included constitutive promoters apFAB61 (SEQ ID NO: 21) and RBS BBa_J61132 (SEQ ID NO: 22) driving the expression of AtzR (sequence optimized for *E. coli* expression). Reporter plasmids were constructed with a plasmid backbone carrying a kanamycin resistant gene and a colE origin of replication. A green fluorescence protein (GFP) was used as the reporter gene and a strong RBS bujard_RBS (SEQ ID NO: 20) was linked to it. Promoters were inserted into the plasmids to drive the expression of the reporter gene. All fragments were amplified with a high-fidelity DNA polymerase (Kapa Bioscience) and plasmids were constructed using isothermal assembly. Assembly reactions were transformed into DH10B *E. coli* cells (NEB) and plated onto LB plates with appropriate antibiotics. After incubating at 37° C. for 16 hours, colonies were sequenced using Sanger sequencing to identify correctly assembled plasmids. Colonies containing correct plasmids were inoculated into 3 mL LB with appropriate antibiotics and grown overnight at 37° C. with constant shaking. Following the overnight growth, cells were miniprepped using a miniprep kit (Omega bioTek) according to the manufacturer's instruction.

Fluorescence measurement: To measure promoter activities, transformed reporter plasmids (including WT promoter plasmid) were transformed into DH10B cells (NEB) using electroporation and plated cells on LB agar plates with kanamycin (50 ug/mL). After overnight growth at 37° C., at least 3 individual colonies were selected for each reporter plasmid and inoculated into 150 μL LB medium with 50 μg/mL kanamycin in a 96-well plate. After 3 hours of growth at 37° C. in a multi-plate shaker (1100 rpm, Southwest Science), cells were diluted 1:50 into 150 μL LB medium or MOPS medium (supplemented with 0.4% glucose and 1× BME vitamin) with 50 μg/mL kanamycin in a 96-well plate. Cells were grown at 37° C. with shaking (1100 rpm). After 16 hours, $OD_{600}$ and fluorescence (excitation at 488 nm and emission at 520 nm with a gain of 40) of each well was measured using a multi-well plate reader (Synergy HTX, BioTek. Inc). Fluorescence was normalized against $OD_{600}$. Blank (normalized fluorescence of cells carrying no GFP) was subtracted from those measurements. Mean and standard deviation of each reporter plasmid activity were calculated from measurements of 3 biological replicates.

To measure fold repression, each reporter plasmid was co-transformed with low and high copy sensor plasmid separately. The end results include two test versions for each reporter plasmid: (the reporter plasmid, low copy sensor plasmid), (the reporter, high copy sensor plasmid), reporter plasmids were transformed with either of the sensor plasmids. Similar to the process of measuring promoter activity, the activities of at least 3 biological replicates were measured for each reporter and sensor plasmid pair. The only difference was that 50 μg/mL kanamycin and 50 μl/mL Spectinomycin were used to maintain both of the reporter and sensor plasmids. The fold repression was calculated as a ratio of the fluorescence of reporter divided by the fluorescence of this reporter when it was paired with a sensor plasmid. To measure fold induction, the process of obtaining fold repression was followed. The only difference was the addition of 200 μM cyanuric acid during the growth. The fold induction was calculated as a ratio of the fluorescence of the induced state divided by the fluorescence of the repressed state.

To obtain transfer functions of various reporter and sensor plasmid pairs, different concentrations of cyanuric acid were delivered via DMSO to cultures (less than 1% of the total volume). After growth for 16 hours, fluorescence was measured and normalized similar to previous experiments.

Visual detection limit: To determine the visual detection limit in LB and MOPS media, *E. coli* DH10B with or without constitutive GFP expression was grown in LB with appropriate antibiotics for 16 hours in a 96-well plate on a shaker (1100 rpm). Two 2 mL aliquots from each culture were spun down at 5000 G for 5 minutes in a benchtop centrifuge at room temperature. The media was aspirated out and the cell pellets resuspended in either 2 mL LB or 2 mL MOPS media. The spin-down and resuspension procedure was repeated two more times. Then, cells without GFP in LB (or MOPS) were mixed with cells carrying GFP in LB (or MOPS) to 150 μL with various ratios (cells without GFP-cells with GFP: 100%-0%, 95%-5%, 90%-10%, 85%-15%, 70%-30%, 55%-45%, 30%-70%, 0%-100%). After measuring the fluorescence and $OD_{600}$ of the mixed cultures in a 96-well plate, the cultures were transferred to ultra-thin strip tubes ordered by increasing percentage of cells carrying GFP. Five individuals were asked to identify the culture that they could be confident to tell apart (in terms of the color of the culture) from the culture containing no cells with GFP (100%-0%). The identification process for cultures in LB and MOPS was performed by placing culture tubes in front of a piece of white paper. The weighted average of fluorescence of cultures was identified by five individuals for cultures in LB and MOPS. The calculated weights averages were defined and used as the visual detection limits in FIGS. 7-10 related experiments.

Optimal conditions for in vivo application: To find the optimal condition(s) for in vivo application of the sensor, the effect of starting $OD_{600}$ on the time needed to reach a net visual detection limit was determined (fluorescence of induced culture-fluorescence of uninduced culture). H6 (high copy sensor plasmid and promoter 6 reporter) was prepared by inoculating a fresh colony into 3 mL LB with 50 μg/mL kanamycin and Spectinomycin. After overnight growth, the culture was inoculated into 300 mL LB with 50 μg/mL kanamycin and Spectinomycin. The culture was grown at 37° C. under shaking (225 rpm, 3 cm radius) until the $OD_{600}$ reached 0.6. Then, the cells in the culture were spun down at 4000 G for 5 minutes. The medium was aspirated out and the cell pellet was resuspended with warm fresh LB (with 50 μg/mL kanamycin and Spectinomycin) to reach $OD_{600}$=18. Following the resuspension, the culture was diluted into other desired $OD_{600}$ with fresh LB (with 50 μg/mL kanamycin and Spectinomycin) and 150 μL of culture was added into each well of a 96-well plate. Various concentrations of cyanuric acid were added via DMSO (<1% volume). The plate was immediately transferred to a multi-well plate reader (Synergy HTX, BioTek. Inc) for continuous shaking at 37° C. The fluorescence of each well was recorded by the plate reader (excitation 448 nm and emission at 520 nm with a gain of 40). The experiment was ended after 12.5 hours of continuous recording. The experiment was performed with four biological replicates.

The net fluorescence increase at a specific time point was calculated by subtracting the fluorescence of the well without cyanuric acid (with the same starting $OD_{600}$) from the fluorescence of the well with cyanuric acid at the specific time point. The time needed to reach a net visual detection limit was at the time point when the net fluorescence increase surpassed the visual detection limit. For wells that never reached a net visual detection limit, the time needed for them to reach a net visual detection limit would be infinity. For the purpose of graphing, the time was set to 12.5 hours (the duration of the recording) for those wells.

SEQ ID NO: 1: Intragenic region between AtzR gene and AtzDEF
ATGCGAGTCAAAGCAAGATCGGTGCCGGATCGGCACCAGTTAGGTCGGAA

AAAGGCGGCAGTCAAGTGCGCAGGGCGGCGTTAAGCTTGAACGAAATGTT

CTGCCTGGGCGCAGTTGCGCCAGGCCGTGTAGTGACGTCGCTCGGTGCAT

GTACAGGGAACAGCCATCCGTCCTATTAACCTTTTTGAGAATTGCCAGAT

SEQ ID NO: 2: WT promoter
ATGCGAGTCAAAGCAAGATCGGTGCCGGATCGGCACCAGTTAGGTCGGAA
AAAGGCGGCAGTCAAGTGCGCAGGGCGGCGTTAAGCTTGAACGAA SEQ ID NO: 3: Promoter 1
ATGCGAGTCAAAGCAAGATCGGTGCCGGATCGGCACCAGTTAGGTCGGAA
AAAGGCGGCAGTCAAGTGCGCAGGGCGGCGTTATAATTGAACGAA SEQ ID NO: 4: Promoter 2
TCGGTGCCGGATCGGCACCAGTTAGGTCGGAAAAAGGCGGCAGTCAAGTG
CGCTTTTTGTACCTATAATAGATTCATGATGA SEQ ID NO: 5: Promoter 3
TCGGTGCCGGATCGGCACCAGTTAGGTCGGAAAAAGGCGGCAGTCAAGTG
CGCTTTTTGTACCTATATAGATTCATGATGA SEQ ID NO: 6: Promoter 4
TCGGTGCCGGATCGGCACCAGTTAGGTCGGAAAAAGGCGGCAGTCAAGTG
CGCTTTTTGTACCTATAAAGATTCATGATGA SEQ ID NO: 7: Promoter 5
TCGGTGCCGGATCGGCACCAGTTAGGTCGGAAAAAGGCGGCAGACAAGTG
CGCTTTTTGTACCTATAATAGATTCATGATGA SEQ ID NO: 8: Promoter 6
TCGGTGCCGGATCGGCACCAGTTAGGTCGGAAAAAGGCGGCAGACAAGTG
CGCTTTTTGTACCTATAATAGATTCATGATGA SEQ ID NO: 9: Promoter 7
TCGGTGCCGGATCGGCACCAGTTAGGTCGGAAAAAGGCGGCAGACAAGTG
CGCTTTTTGTACCTATATAGATTCATGATGA SEQ ID NO: 10: Promoter 8
TCGGTGCCGGATCGGCACCAGTTAGGTCGGAAAAAGGCGGCAGACAAGTG
CGCTTTTTGTACCTATAAAGATTCATGATGA SEQ ID NO: 11: Promoter 9
TCGGTGCCGGATCGGCACCTGACAGGTCGGAAAAAGGCGGCTATAAGTGC
GCATGATGA SEQ ID NO: 12: Promoter 10
TTGACAGGTGCCGGATCGGCACCTATAATAGATTCATGATGA SEQ ID NO: 13: Promoter 11
CAAGATCGGTGCCGGATCGGCACCAGTTAGGTCTTGACATCGCATCTTTT
TGTACCTATAATAGATTCATGATGA SEQ ID NO: 14: Promoter 12
GGTGCCGACACGGCACCTTTTTGTACCTATAATAGATTCATGATGA SEQ ID NO: 15: Promoter 13
TTGACAGGTGCCGATCCGGCACCTATAATAGATTCATGATGA SEQ ID NO: 16: Promoter 14
GACCTAACTGGTGCCGATCCGGCACCGATCTTGTTGACATCGCATCTTTT
TGTACCTATAATAGATTCATGATGA SEQ ID NO: 17: Promoter 15
GGTGCCGATCCGGCACCTTGACATCGCATCTTTTTGTACCTATAATAGAT
TCATGATGA SEQ ID NO: 18: Promoter 16
GGTGCCGATCCGGCACCTTTTTGTACCTATAATAGATTCATGATGA SEQ ID NO: 19: apFab71
TTGACATCGCATCTTTTTGTACCTATAATAGATTCATGATGA SEQ ID NO: 20: Bujard_RBS
GAATTCATTAAAGAGGAGAAAGGT SEQ ID NO: 21: apFab61
TTGACAATTAATCATCCGGCTCGTTTAATAGATTCATTAGAG SEQ ID NO: 22: Bba_J61132
TCTAGAGAAAGACAGGATTAAC

RBS-L
GGTGCCG

RBS-R
CGGCACC

ABS-1
GGTCGG

ABS-2
GGCGGC

ABS-3
AGTGCG

SEQ ID NO: 23: DNA sequence optimized (for E. coli) AtzR
ATGCAACACCTGCGTTTCCTGCACTACATCGACGCGGTTGCGCGTTGCGG

TAGCATCCGTGCGGCGGCGGAGCAACTGCATGTTGCGGCGAGCGCGGTGA

ACCGTCGTGTTCAAGATCTGGAGTACGAACTGGGTACCCCGATCTTTGAG

CGTCTGCCGCGTGGTGTGCGTCTGACCGCGGCGGGTGAACTGTTTGTTGC

GTATGCGCGTCGTCGTAACGCGGACCTGGAACAGGTGCAAAGCCAGATTC

AAGATCTGAGCGGTATGAAGCGTGGCCGTGTTACCCTGGCGGCGAGCCAG

GCGCTGGCGCCGGAGTTCCTGCCGCGTGTGATCCACGCGTTTCAGGCGCA

ACGTCCGGGTATTGCGTTCGACGTGAAAGTTCTGGATCGTGAACGTGCGG

TGCTGGCGGTTACCGACTTTGCGGCGGATCTGGCGCTGGTGTTTAACCCG

CCGGACCTGCGTGGCCTGACCGTTATTGCGCAGGCGCGTCAACGTATTTG

CGCGGTGGTTGCGAGCGATCACCCGCTGGCGAAGCGTACCAGCCTGCGTC

TGAAAGACTGCCTGGATTACCCGCTGGCGCTGCCGGACAGCAGCCTGAGC

GGTCGTAACGTGCTGGACGAGCTGTTTGATAAAAGCAGCGCGCGTCCGCG

TCCGCAGCTGGTTAGCAACAGCTATGAGATGATGCGTGGCTTCGCGCGTG

AAACCGGTGGCGTGAGCTTTCAAATCGAAATTGGTGCGGGCAGCACCGAG

GGTGAAGTTGCGATCCCGATTGATGAGCGTAGCCTGGCGAGCGGCCGTGT

GGTTCTGGTTGCGCTGCGTGAACGTGTGCTGCCGGTTGCGAGCGCGGCGT

TTGCGGAGTTCGTTGCGGGCAAGCTGGCGGATACCACCCATAATGCGACC

TAA

Example 1: Design and Activation of Promoter Variants

The intergenic region atzR-DEF is a pair of divergent promoters, PatzDEF and PatzR, regulating the expression of the TF atzR and the catabolic operon atzDEF (FIG. 1). There are five known AtzR binding sites in the intergenic region: two repressor binding sites (RBS L and R) and three activator binding sites (ABS 1, 2 and 3) (FIG. 1). AtzR binds more tightly to RBS than ABS. It has been proposed that one dimer of an AtzR tetramer binds to RBS and other the dimer to ABS 2 and 3 to induce DNA bending. This covers up the $\sigma^{70}$ binding sites of PatzDEF located on either side of ABS 3 and a part of the spacer resulting in transcription repression. When AtzR binds to cyanuric acid, one of the dimers undergoes a conformational change and binds to ABS1 and 2 instead of ABS 2 and 3, thereby exposing $\sigma^{70}$ sites for transcription initiation. Also, the change in binding site preference (ABS 2 and 3 to ABS 1 and 2) induces relaxation in DNA bending and moves the bending from between ABS 1 and 2 to the region between RBS-R and ABS 1. The change is proposed to be the major driver for transcription activation of PatzDEF. At the other end of the divergent promoter, AtzR is autorepressed at PatzR. The $\sigma^{54}$ binding sites of PatzR are on the complementary strain of the DNA and RBS-R overlaps with a putative NtrC binding half site.

Based on these observations, a sensor plasmid (carrying AtzR) was constructed in which AtzR was placed under the control of a strong constitutive promoter (apFAB61, SEQ ID NO: 21) and a strong RBS (BBa_J61132; SEQ ID NO: 29). This removed autoregulation and nitrogen-dependent expression of AtzR. Next, two groups of promoter variants were constructed that broadly preserved the overall architecture (number and ordering of atzR binding sites) of the native *Pseudomonas* promoter (FIG. 2): group 1 promoters were based on PatzDEF and group 2 promoters were based on PatzR. To make the native *Pseudomonas* promoters compatible with *E. coli*, a strong, constitutive $\sigma^{70}$-dependent promoter (apFab71) was embedded either partially or fully within PatzDEF and PatzR. ApFab71 is a synthetic *E. coli* promoter with canonical −35 and −10 $\sigma^{70}$ binding sites, a 17 bp spacer between them, a short discriminator, and 25 bp of 5' UTR containing a strong ribosome binding site (Bujard RBS).

Figure 2:
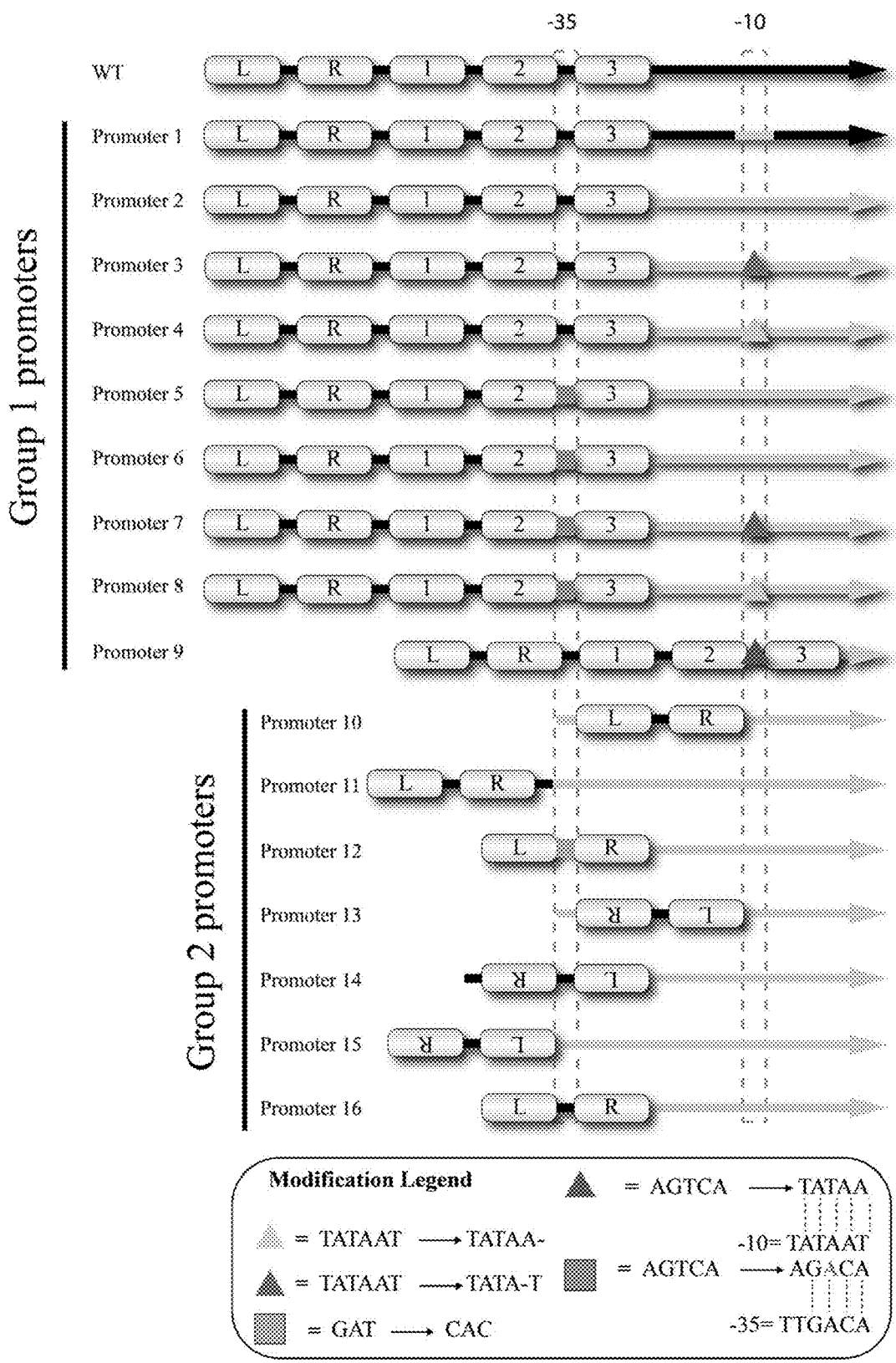
FIG. 2 shows the design of promoter variants for porting wildtype *Pseudomonas* promoter into *E. coli*. Group I promoter variants contain both ABS and RBS, while group 2 variants contain only RBS.

Eight group 1 and six group 2 promoters were tested in addition to the wildtype promoter. In wildtype PatzDEF, the −35 site is located between ABS 2 and 3 and the −10 site is located downstream of ABS 3 (FIG. 2). All group 1 promoter variants preserved this arrangement. Without being held to theory, we hypothesized that a strong *E. coli* $\sigma^{70}$-10 site for could be sufficient for promoter activity, and therefore replaced *Pseudomonas*-10 site with consensus *E. coli* for $\sigma^{70}$ binding −10 site (TATAAT) to design promoter variant 1. In promoter variant 2, the entire sequence 3' of the ABS 3 in the native promoter (starting at 5' end of the conserved *Pseudomonas* sp $\sigma^{70}$-10 region) was replaced with a loosely corresponding region of apFab71 (starting at 5' end of the conserved *E. coli* $\sigma^{70}$-10 region. In case the baseline expression of promoter variants 1 and 2 is too high, which may decrease the dynamic range of the biosensor, promoters 3 and 4 were designed to weaken promoter strength by deleting single bases from the −10 site (FIG. 2). Promoter variants 7 and 8 of presumed intermediate strength were designed by mutating the *Pseudomonas* native −35 site to more closely resemble a consensus *E. coli* $\sigma^{70}$-35 site (TTGACA). Promoter variants 5 and 6 were designed to be the strongest in group 1 containing consensus *E. coli* $\sigma^{70}$-35 and entire sequence 3' of apFab71 (starting at 5' end of the conserved *E. coli* $\sigma^{70}$-10 region). Promoter variant 5 was on a high-copy number plasmid and promoter variant 6 on a low-copy number plasmid.

In group 2, the location and the orientation of the RBS within or flanking apFab1 were varied (FIG. 2) to create seven promoter variants resembling PatzR. Within group 2, four promoter variants (10, 11, 12 and 16) were designed with RBS in the L-R orientation and three promoter variants (12, 13 and 14) in the R-L orientation. The spacing between L and R sites was kept fixed in all variants. To tightly repress gene expression, promoters 10 and 13 were designed by replacing the spacer of apFAB1 with RBS L and R (in both orientations) such that AtzR bound to RBS would directly block the RNA polymerase from accessing −35 and −10 sites. Because a tightly repressed promoter may not provide high reporter signal upon induction, promoters 11 and 15 were designed by placing the RBS upstream of −35 to provide the RNA polymerase partial access to its binding site. Promoters of presumed intermediate repression were designed (promoter variants 14 and 16) by placing the −35 site between RBS L and R in both orientations. All group 1 and 2 promoter variants were followed by a strong ribosome binding site (Bujard RBS) driving the expression of GFP.

Figure 3:
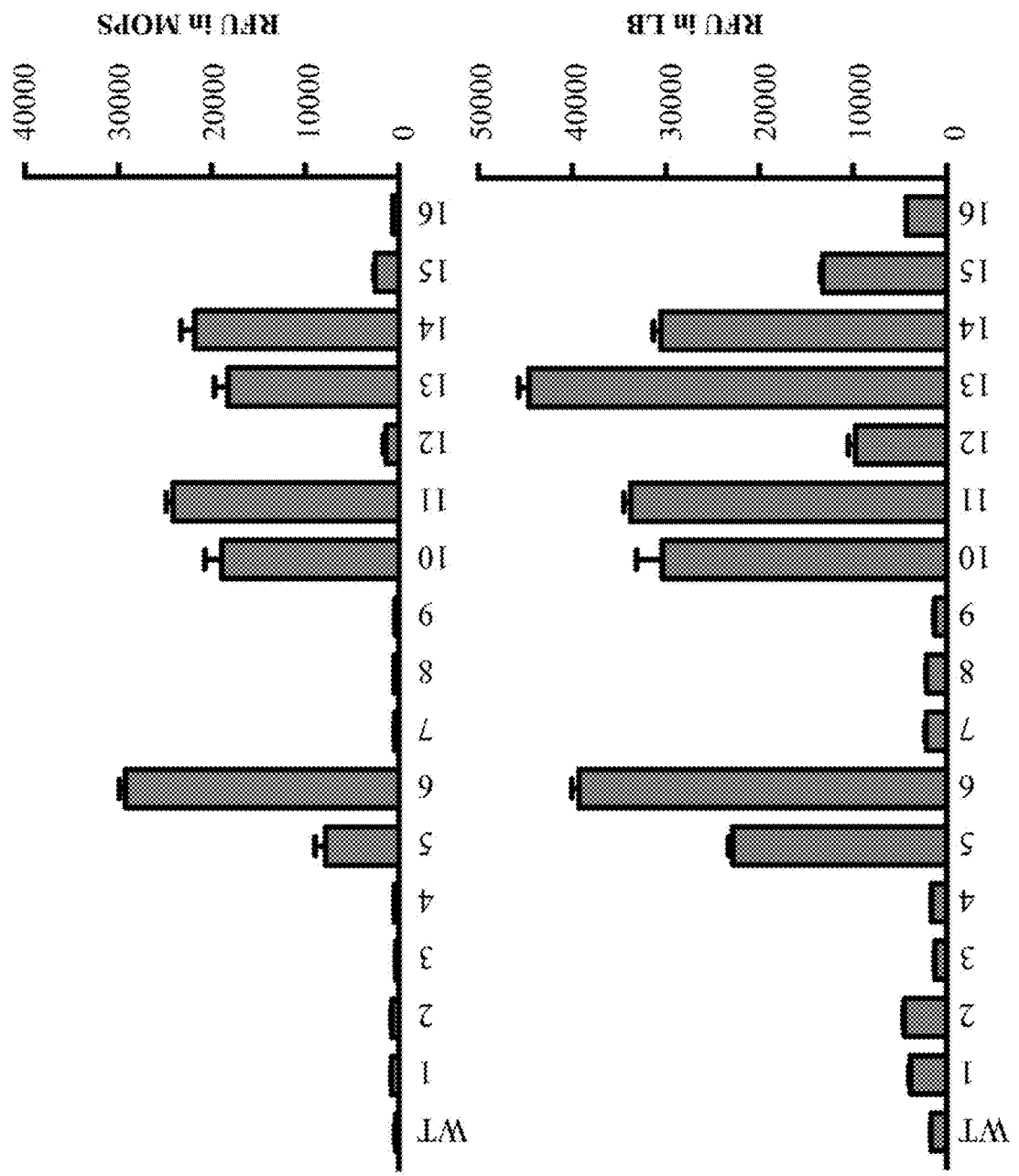
FIG. 3 shows promoter variant activity measured as a constitutively expressed GFP reporter in LB and MOPS media. AtzR is not present. RFU is relative fluorescence units. Blanks were subtracted from measurements.

GFP reporter expression of *E. coli* cells carrying only the promoter (no AtzR present) grown in both rich and minimal media was measured. We tested in both media because LB is most common medium type and provide nutrient rich environment for cells to grow while minimal medium such as MOPS can provide a lower background noise. The expression varied over 100-fold across all promoter variants (FIG. 3). Nearly all promoter variants (13/16 in LB and 16/16 in minimal media) were transcriptionally active and gave higher GFP signal than the wildtype promoter in LB suggesting that our design strategy was successful in a porting a *Pseudomonas* promoter into *E. coli*. Group two promoters generally gave substantially higher GFP expression than group one possibly because group 2 promoter variants more closely matched an intact apFab1 than group 1. Among group 2 promoter variants, the orientation of RBS L and R did not have an appreciable impact on promoter activity (compare 10, 11, 12 and 16 vs. 13, 14 and 15). The highest expression was observed in promoters 7 and 8 among group 1 because they closely resemble an intact apFab1 including a consensus $\sigma^{70}$-10 site and a near-consensus $\sigma^{70}$-35 site. Our promoter designs captures a wide range of expression levels and that potentially allows us to find functionally biosensors with different baseline and induction levels.

Example 2: AtzR-Dependent Activation of Promoter Variants

Figure 4:
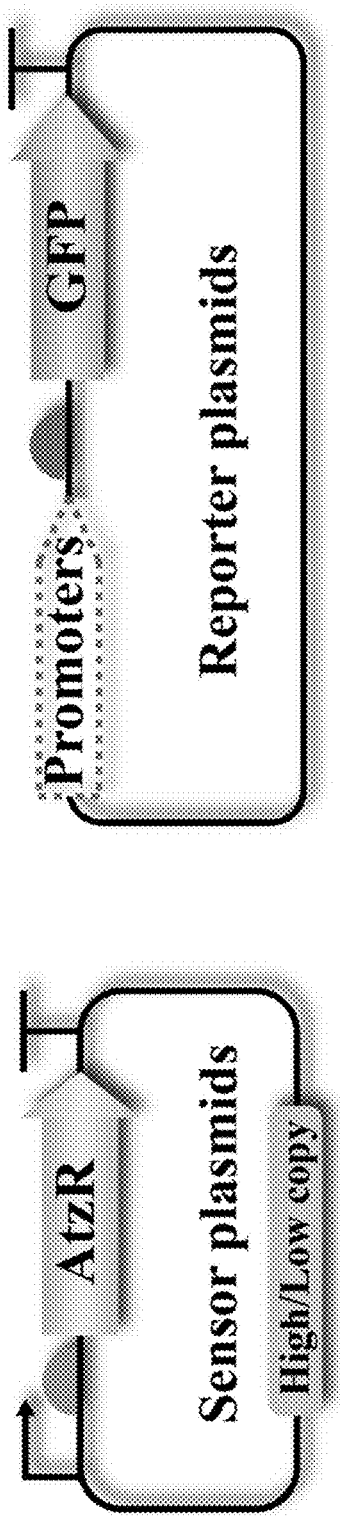
FIG. 4 shows a schematic of a dual plasmid system. The sensor plasmid expresses AtzR from a constitutive *E. coli* promoter and the reporter plasmid expresses GFP from a designed promoter variant responsive to AtzR. Both high and low copy versions of the sensor plasmid were constructed.
Figure 5:
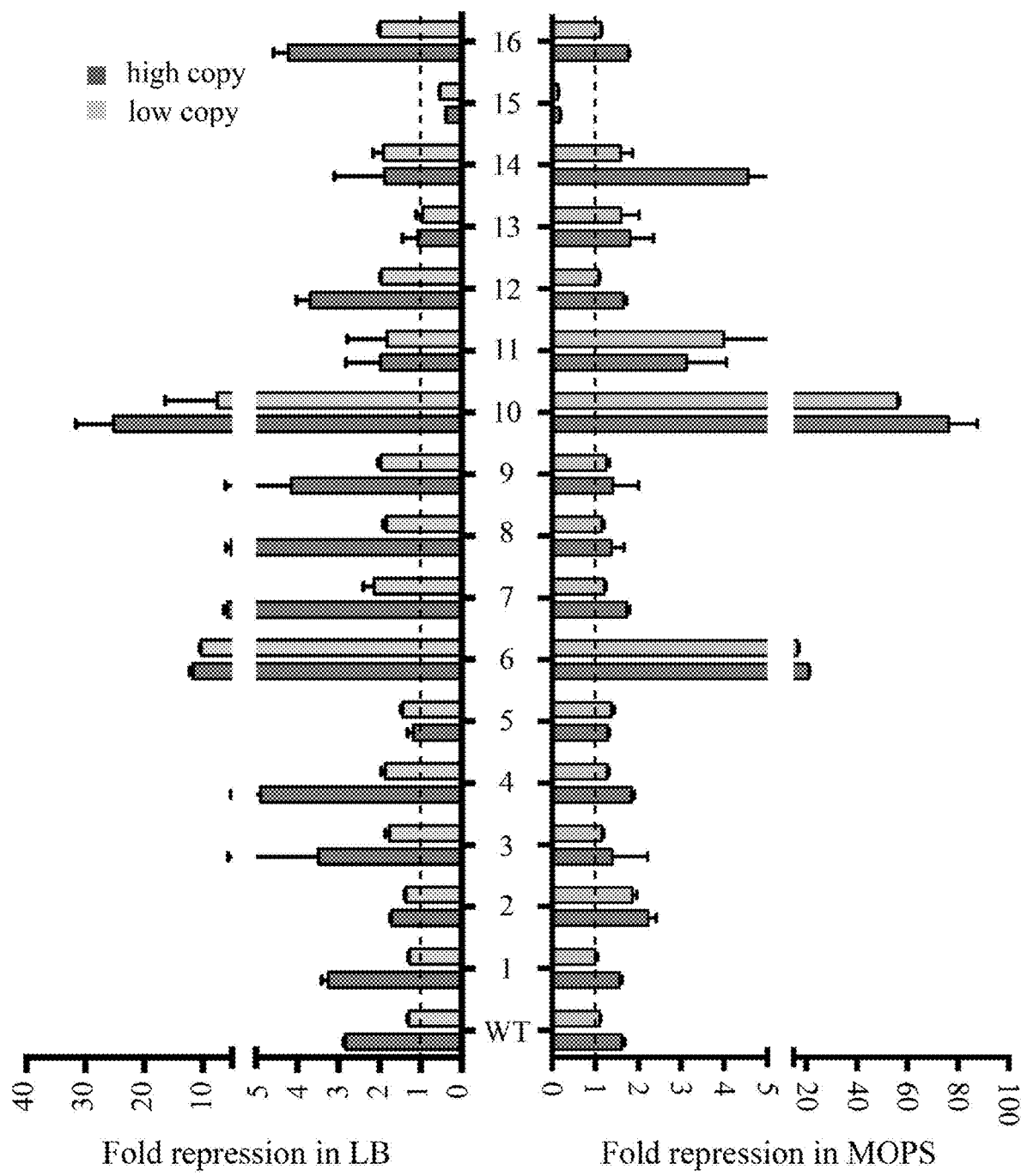
FIG. 5 shows the fold change ration of GFP expression in cells carrying a promoter variant without or with co-expressed AtzR for wildtype and 16 promoter variants.

AtzR was co-expressed from a constitutive promoter on a different plasmid together with each promoter variant. Since the concentration of TF is an important determinant of signal response, AtzR was expressed from both low- and high-copy number (approximately 5 copies per cell and approximately 50 copies per cell, respectively) plasmids (FIG. 4). The fold repression of all 16 promoter variants was measured, including wildtype with either low- or high-copy plasmids carrying AtzR in either rich or minimal media. Fold repression is defined as the ratio of GFP expression without and with AtzR; higher fold repression implies greater loss of GFP expression when AtzR is expressed. The vast majority of promoters (11 (SEQ ID: 3, 4, 5, 7, 11, 13, 14, 15, 16, 17 and 18) out of 16 in rich and 14 (SEQ ID: 3, 4, 5, 6, 7, 9, 10, 11, 13, 14, 15, 16, 17 and 18) out of 16 in minimal medium, respectively) were repressed less than 5-fold even at high AtzR concentration (FIG. 5). Although AtzR expressed from a high-copy plasmid consistently gave slightly higher fold repression than from a low-copy plasmid, the differences were not appreciable. Fold repression of nearly all group 1 promoters was small suggesting that simply overexpressing AtzR does not alter its known mechanism as a transcription activator to a transcription repressor. However, promoter variant 10 (50-fold repression in minimal medium, group 2) and promoter variant 6 (10-fold repression in minimal medium, group 1) are exceptions. The architecture of promoter variant 10 closely resembles a canonical repressor where the palindromic half sites are located between the −35 and −10 sites. RBS L and R of promoter 9 are positioned optimally for AtzR to compete with $\sigma^{70}$ binding to the promoter.

Example 3: Activation of AtzR Biosensor with Cyanuric Acid

Figure 6:
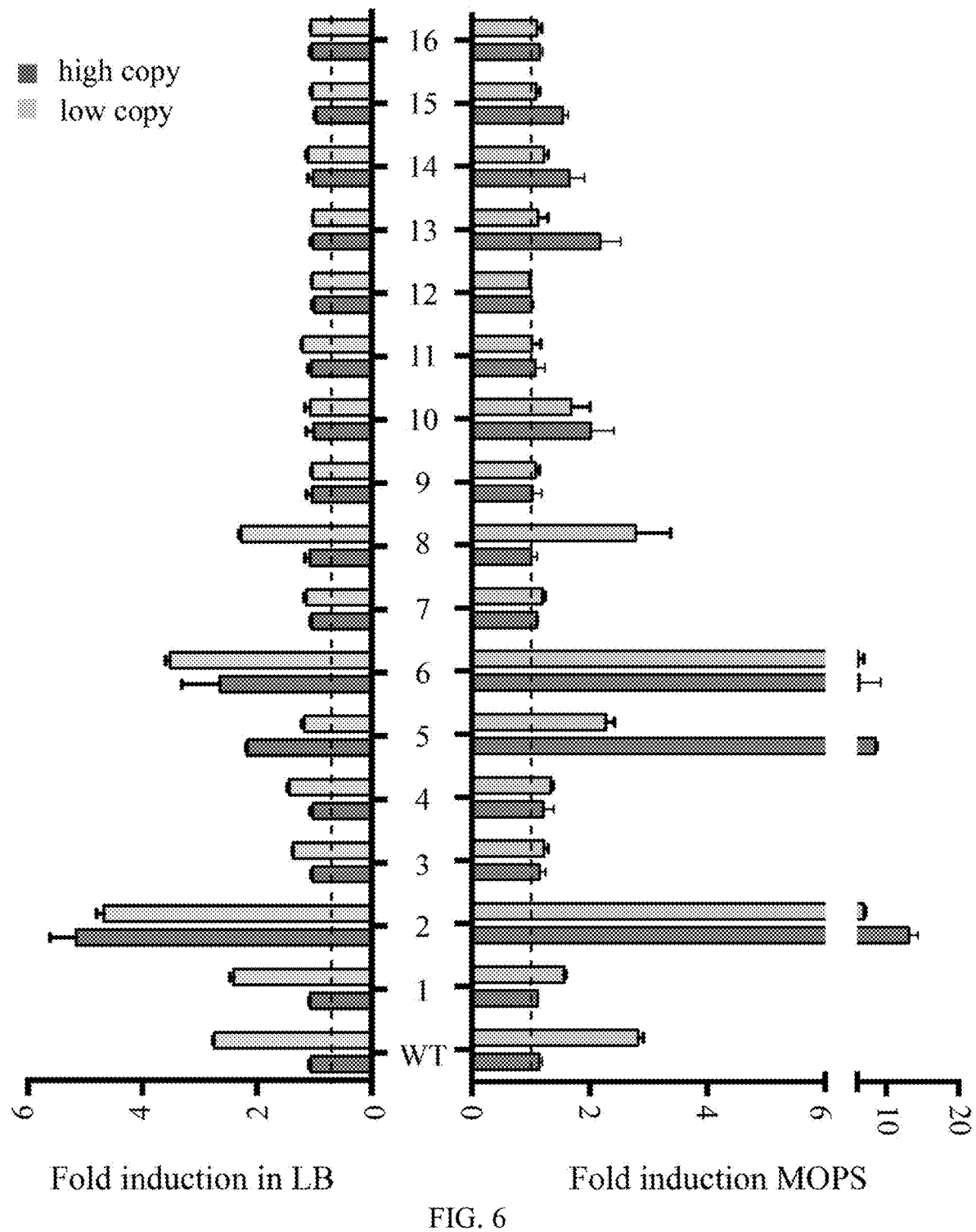
FIG. 6 shows the fold change ration of GFP expression in cells carrying a promoter variant with co-expressed AtzR with and without cyanuric acid (200 μM) in the medium for wildtype and 16 promoter variants. Black dashed line marks fold change of one, i.e., no change in GFP expression. Experiments were carried out in LB (purple) and MOPS media (red) with AtzR expressed from high (dark shade) and low copy (light shade) number plasmids.
Figure 7:
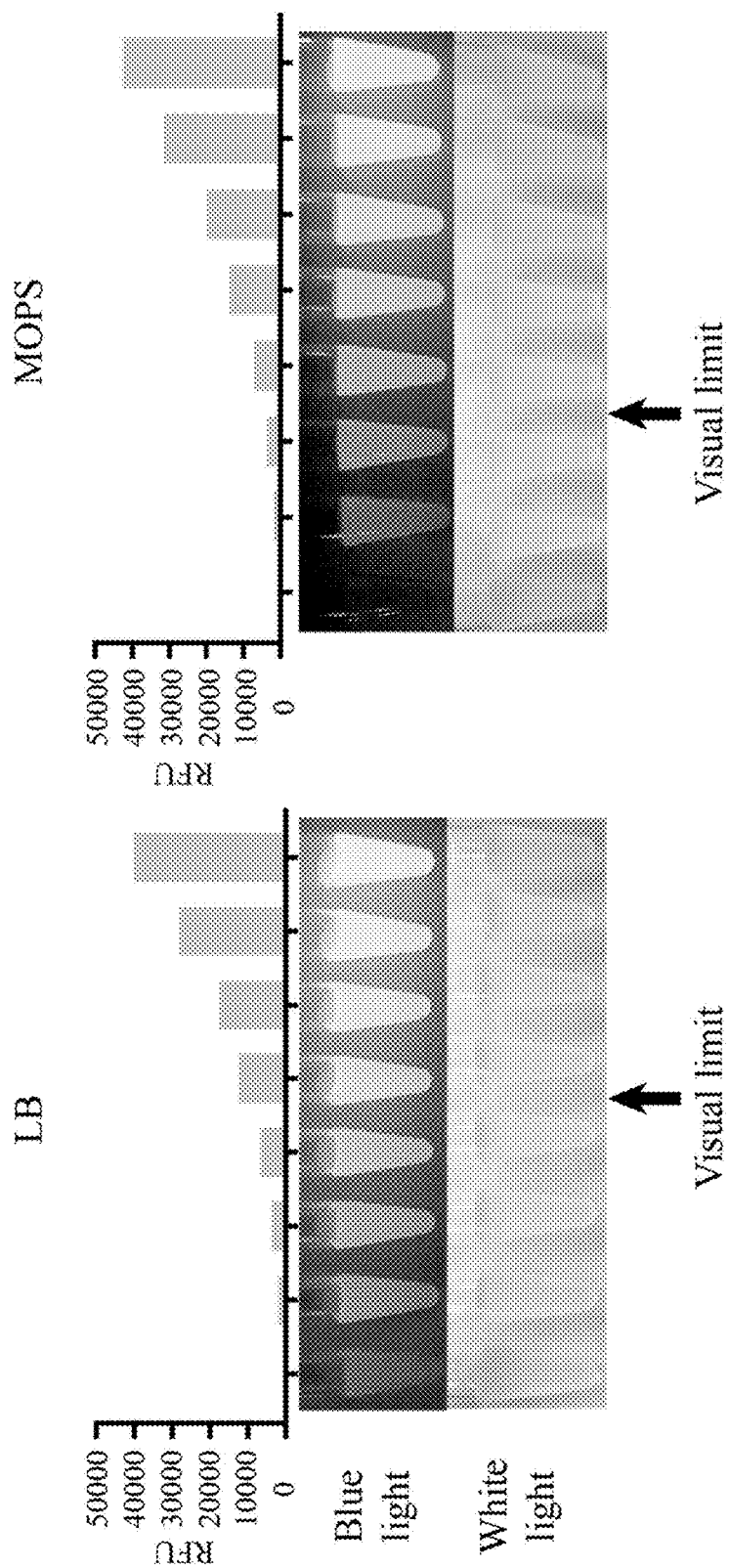
FIG. 7 shows the determination of the threshold for visually detectable fluorescence signal in cells grown in LB (left) and MOPS (right). The threshold was estimated after surveying multiple individuals to choose their visual limit of detection from a dilution series of GFP expressing cells.

The cyanuric acid response of each promoter variant was measured by inducing cells co-expressing AtzR with 200 μM cyanuric acid. 200 μM (25 ppm) was chosen because this is near the lower bound for cyanuric acid concentration in a swimming pool. The fold activation was evaluated, which is the ratio of GFP with and without cyanuric acid, of all promoters in all four conditions: AtzR concentration (high and low) and medium (rich and minimal) (FIG. 6). Several group 1 promoter variants responded to cyanuric acid. In particular, promoter variants 2, 5 and 6 were activated near 10-fold, with promoter 2 giving highest fold activation (15-fold) in minimal media. All three promoter variants contain strong *E. coli* $\sigma^{70}$ elements including a consensus −10 site and gave higher fold activation in minimal than rich media. Although promoter variants 2, 3 and 4 are nearly identical with differences in −10 site, only promoter variant 2 was inducible. This suggests that an intact −10 site (promoter variant 2) may be essential for ligand-dependent transcription. Wildtype and its minimally modified version (promoter 1) gave low fold activation (<3.0-fold). While the fold activation of promoter variants 2 and 5 are comparable (approximately 10-fold), their reporter dynamic ranges are completely different. The uninduced baseline (no cyanuric acid) of promoter variant 2 is about 4000 fluorescence units while that of promoter variant 5 is 22000 fluorescence units. In contrast to group 1, none of the group 2 promoters responded to cyanuric acid. The lack of cyanuric acid response from promoter 10 of group 2, which was highly repressed by AtzR, suggests that either cyanuric acid does not induce when AtzR acts as a repressor or that the concentration of cyanuric acid was insufficient. From the results so far, we can conclude that having a housing keep sigma factor promoter architecture and intermediate basal expression level is the key for designing a transcription activation circuit.

Example 4: Visual Detection of Cyanuric Acid with AtzR Biosensor

Next, the biosensor was evaluated for sensing cyanuric acid by visual detection of the reporter. The fluorescence intensity of cells expressing GFP required for unambiguous detection by the naked eye (arrows in FIG. 7 and dashed lines in FIG. 8 and FIG. 9) was estimated. Due to autofluorescence of rich media, the visual detection threshold in rich media is greater than minimal media. Based on fold activation (FIG. 6), the top three promoters were chosen (promoters 1, 2 and 15), two weaker promoters (11 and 16) and the wildtype for evaluation. AtzR was co-expressed on a high-copy plasmid (promoter 1), both high- and low-copy plasmids (promoters 2 and 15), or only on a low-copy plasmid (promoters 11, 16 and wildtype). The GFP dose-response was measured over cyanuric acid concentrations from 0 to 1 mM of cells grown in rich and minimal media. The lower threshold of detection for all three top promoters (1, 2 and 15) was ~25 uM and ~15 uM in rich and minimal media, respectively. Promoters 1, 2 and 15 gave a net visually detectable GFP signal above 75 uM (11 ppm) and 50 uM (7 ppm) cyanuric acid concentration in rich and minimal media, respectively, with the signal beginning to saturate at 1 mM (125 ppm). In rich media, the sigmoidal region of the dose-response curve where concentration differences are well resolved lies between 50-750 uM. The slope of sigmoid region is steeper in minimal media although the lower and upper limits of detection is similar to rich media (50-750 uM). These results show that detection range of the biosensor lies within the limits of cyanuric acid concentrations normally found in swimming pools (200-600 μM).

Example 5: Kinetics of AtzR Biosensor Response

Figure 10:
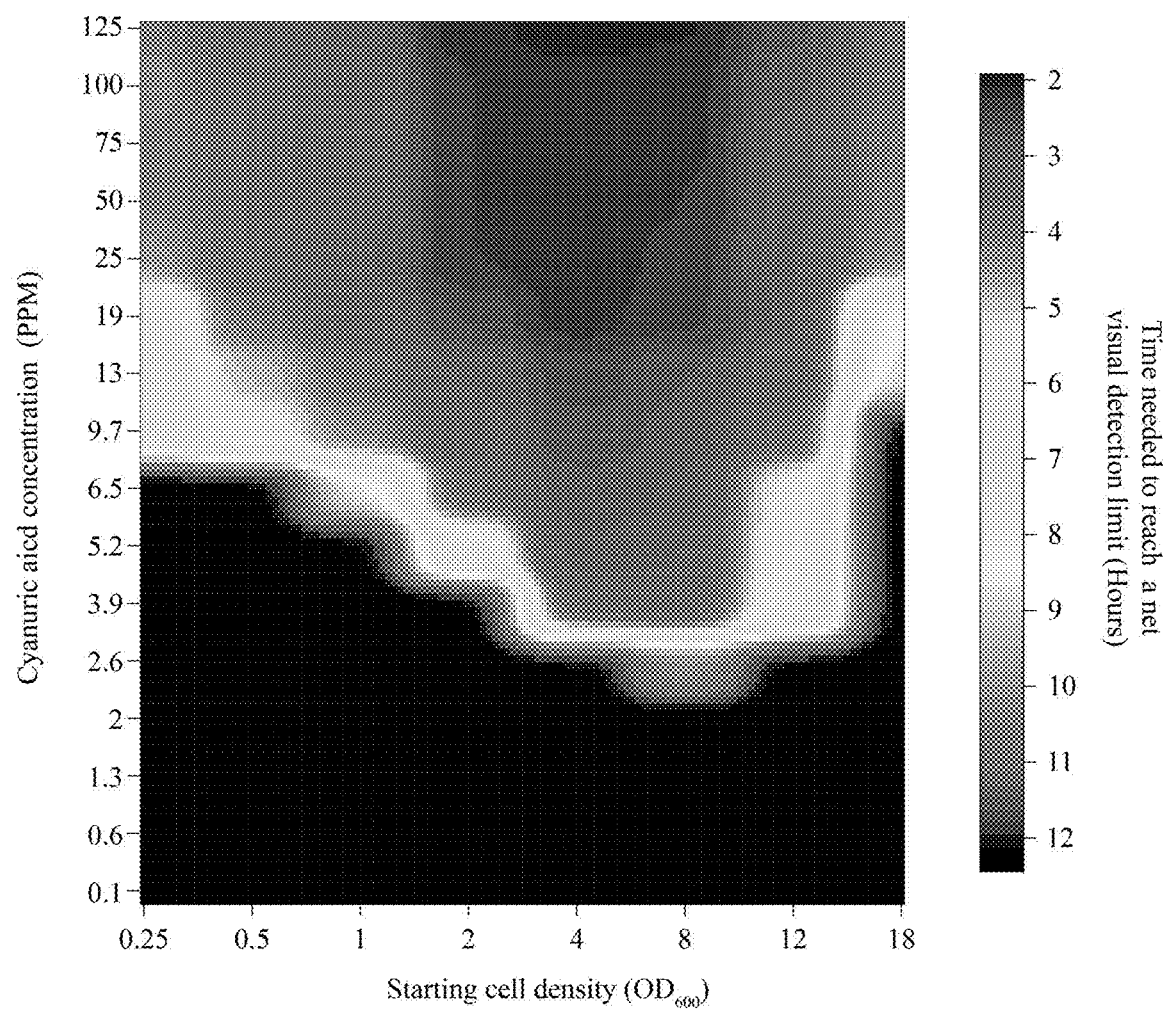
FIG. 10 shows the kinetics of biosensor response for real time cyanuric acid detection. Time required for each net visual detection threshold (no cyanuric acid control subtracted) for varying starting cell densities and cyanuric acid concentrations. The fastest response time of approximately 2 hours at lowest cyanuric acid concentration was achieved at a starting OD600 of approximately 4.0.

To assess the suitability of AtzR biosensor in a field application, the time required for an accurate visual readout was estimated. First, the type of the promoter variant driving reporter expression will have direct effect on how effectively the output can be visually detected. A promoter variant with low baseline activity and high fold activation with ligand would be desirable because reporter fluorescence can be accurately quantified (e.g: L2 in FIG. 8, 9). However, for visual detection with the naked eye, a promoter variant that produces a large amount of the reporter, even if the baseline is higher, would enable reaching the visual detection limit in the shortest time (For e.g: H5 and H6 in FIG. 8,9). Second, the growth medium is also important. By and large, cells grown in minimal media give higher fold induction than cells grown in LB most likely due to the low background fluorescence in minimal medium. However, using cells grown in minimal media is impractical due longer growth times, lower reporter intensity and cost. Third, optimal starting cell density (measured in OD600) is an important factor in time required for detectable signal. A low starting cell concentration can take a long time to accumulate enough cell density and reporter concentration. On the other hand, if the starting cell concentration is too high, the background fluorescence could be higher and cells might enter semi-anaerobic condition resulting in attentuated transcription and translation. To find the optimal range of starting cell density, the time required to reach a net visual detection limit (difference between fluorescence of induced culture and fluorescence of uninduced culture) was measured in LB under a wide range of starting cell densities (0.25-18) and cyanuric acid concentration (0.1-125 PPM) (FIG. 10). Promoter/sensor variant H6 (see FIG. 8, 9) since it gave maximum reporter output.

Figure 8:
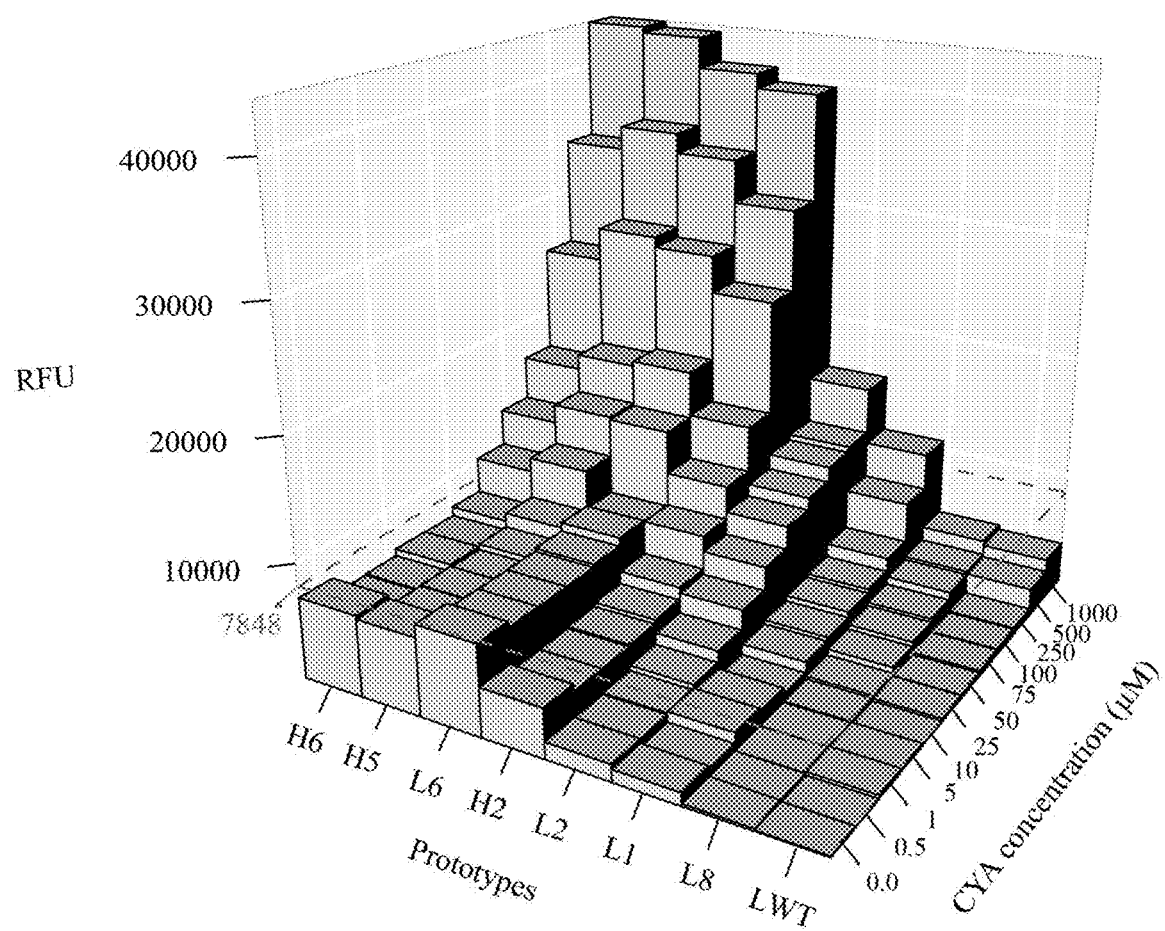
FIG. 8 shows dose response curves (0-1 mM) of best performing variants in LB media. Promoter variant number and sensor plasmid copy number are indicated. For example, H6 is promoter variant 6 with AtzR expressed from a high copy number plasmid.
Figure 9:
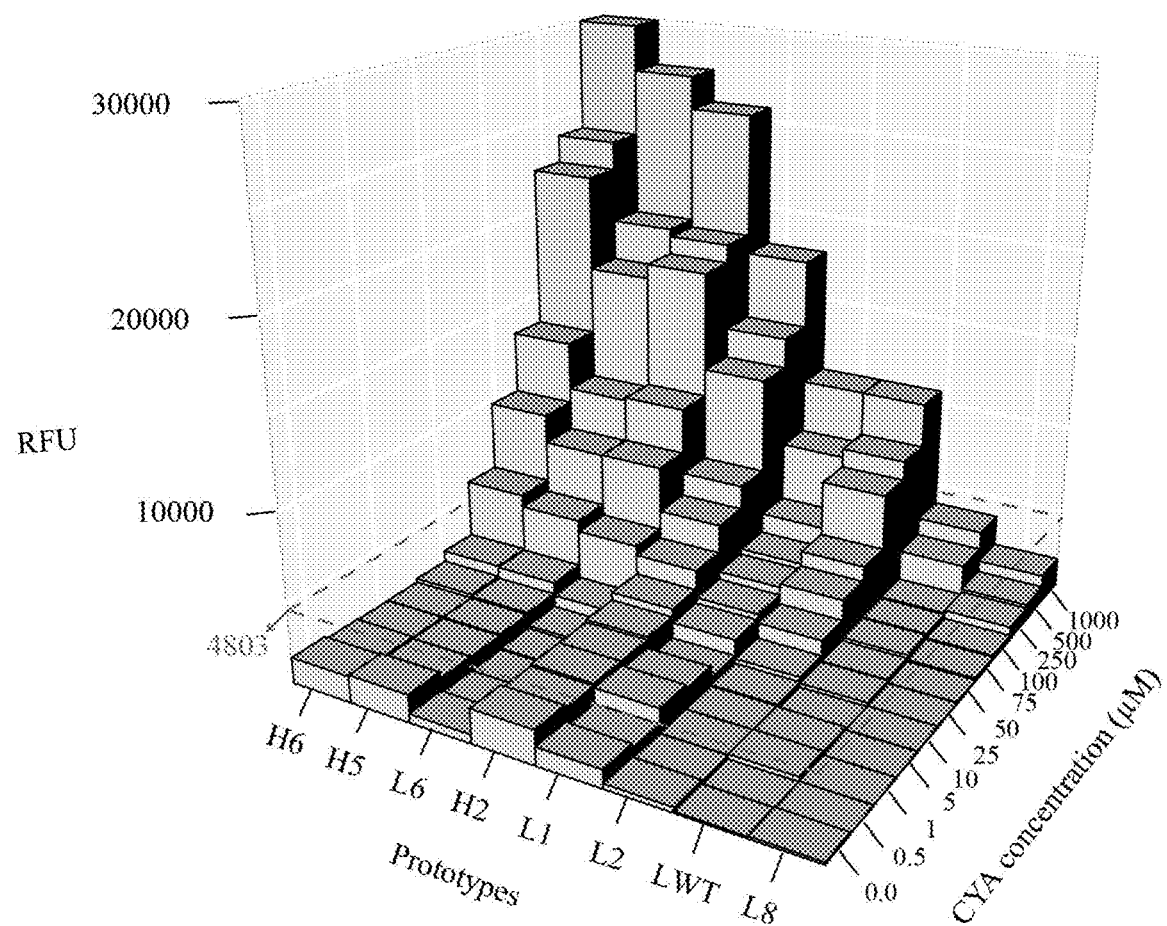
FIG. 9 shows dose response curves (0-1 mM) of best performing variants in MOPS media.

The fastest response time to visual detection at the lowest concentration of cyanuric acid was two hours at 20 ppm at a moderate cell density of approximately OD600 8.0. Over a two-fold increase time was needed when cell concentration was lower than 0.5 or higher than 12 (OD600) at 20 ppm, suggesting that a moderate cell density is optimal. It is consistent with the prediction that neither low nor high cell concentration would be ideal for the assay. It was also observed that the optimal cell concentrations allowed for lower detection range (using time needed to a net visual detection limit). 2, 4 and 8 ($OD_{600}$) on average allowed detection down to 4 ppm cyanuric acid while 0.5 or 18 (OD600) only allowed detection down to around 10 ppm. Furthermore, reduced time was observed as the concentration of cyanuric acid increased within given starting cell concentration. It comes no surprise as a higher concentration of cyanuric acid is conducive to a higher induction level (FIG. 8, 9). The mapping of the starting cell concentration and cyanuric concentration can be very helpful when comes to determining cyanuric concentration in a test sample using various starting cell concentrations or dilutions of the test sample for cross validations.

For conditions that never reached a net visual detection limit, their time was set to 12.5 hours (the end point of the experiment).

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A cyanuric acid-responsive biosensor, comprising an *E. coli* host strain or an *E. coli* cell-free system comprising a first and a second expression cassette, the first expression cassette comprising, in operable communication, a constitutive promoter and a gene encoding a *Pseudomonas* sp. AtzR cyanuric acid-responsive transcription factor, and the second expression cassette comprising, in operable communication, a promoter regulated by the AtzR cyanuric acid-responsive transcription factor and a gene encoding a reporter protein, wherein the first expression cassette expresses the AtzR cyanuric acid-responsive transcription factor, and, in the presence of cyanuric acid, the AtzR cyanuric acid-responsive transcription factor drives expression of the reporter protein, wherein the promoter regulated by the AtzR cyanuric acid-responsive transcription factor is a modified atzR-DEF promoter from a *Pseudomonas* sp. comprising an *E. coli*-10 sequence, an *E. coli*-35 sequence or both, and a 3' *E. coli* constitutive $\sigma^{70}$-dependent promoter, wherein the *E. coli*-10 sequence is TATAAT, the *E. coli*-35 sequence is TTGACA, and the 3' *E. coli* constitutive $\sigma^{70}$-dependent proomoter is SEQ ID NO: 19.

2. The cyanuric acid-responsive biosensor of claim 1, wherein the first expression cassette and the second expression cassette are present on the same or different DNA molecules.

3. The cyanuric acid-responsive biosensor of claim 1, wherein the first expression cassette is present in a high or low copy number sensor plasmid, and the second expression cassette is present on a reporter plasmid.

4. The cyanuric acid-responsive biosensor of claim 1, wherein the promoter regulated by the AtzR cyanuric acid-responsive transcription factor comprises SEQ ID NO. 3, 4, 7, 8, or 10.

5. The cyanuric acid-responsive biosensor of claim 1, wherein the *E. coli* is grown in rich or minimal media.

6. The cyanuric acid-responsive biosensor of claim 5, having a detection time of about 2 hours at an optical density of 2-8.

7. The cyanuric acid-responsive biosensor of claim 1, having a lower detection limit of about 5 μM (or about 0.6 PPM) cyanuric acid, and an upper detection limit of about 750 μM (or about 94 PPM).

8. The cyanuric acid-responsive biosensor of claim 1, wherein the reporter protein comprises GFP or FbFP.

9. The method of claim 4, wherein the constitutive promoter of the first expression cassette comprises SEQ ID NO: 21.

10. A cyanuric acid-responsive biosensor, comprising
an *E. coli* host strain or an *E. coli* cell-free system comprising a first and a second expression cassette,
the first expression cassette comprising, in operable communication, a constitutive promoter and a gene encoding a *Pseudomonas* sp. AtzR cyanuric acid-responsive transcription factor, and
the second expression cassette comprising, in operable communication, a promoter regulated by the AtzR cyanuric acid-responsive transcription factor and a gene encoding a reporter protein,
wherein the first expression cassette expresses the AtzR cyanuric acid-responsive transcription factor, and, in the presence of cyanuric acid, the AtzR cyanuric acid-responsive transcription factor drives expression of the reporter protein, wherein the promoter regulated by the AtzR cyanuric acid-responsive transcription factor comprises SEQ ID NO. 3, 4, 7, 8, or 10.

11. The cyanuric acid-responsive biosensor of claim 10, wherein the first expression cassette and the second expression cassette are present on the same or different DNA molecules.

12. The cyanuric acid-responsive biosensor of claim 10, wherein the first expression cassette is present in a high or low copy number sensor plasmid, and the second expression cassette is present on a reporter plasmid.

13. The cyanuric acid-responsive biosensor of claim 10, wherein the *E. coli* is grown in rich or minimal media.

14. The cyanuric acid-responsive biosensor of claim 13, having a detection time of about 2 hours at an optical density of 2-8.

15. The cyanuric acid-responsive biosensor of claim 10, having a lower detection limit of about 5 μM (or about 0.6 PPM) cyanuric acid, and an upper detection limit of about 750 μM (or about 94 PPM).

* * * * *

SEQUENCE LISTING

```
<160> NUMBER OF SEQ ID NOS: 23

<210> SEQ ID NO 1
<211> LENGTH: 200
<212> TYPE: DNA
<213> ORGANISM: Artificial Sequence
<220> FEATURE:
<223> OTHER INFORMATION: Intragenic region between AtzR gene and AtzDEF

<400> SEQUENCE: 1
atgcgagtca aagcaagatc ggtgccggat cggcaccagt taggtcggaa aaaggcggca       60
gtcaagtgcg cagggcggcg ttaagcttga acgaaatgtt ctgcctgggc gcagttgcgc      120
caggccgtgt agtgacgtcg ctcggtgcat gtacagggaa cagccatccg tcctattaac      180 cttttgaga attgccagat                                                   200

<210> SEQ ID NO 2
<211> LENGTH: 95
<212> TYPE: DNA
<213> ORGANISM: Artificial Sequence
<220> FEATURE:
<223> OTHER INFORMATION: WT promoter

<400> SEQUENCE: 2
atgcgagtca aagcaagatc ggtgccggat cggcaccagt taggtcggaa aaaggcggca       60
gtcaagtgcg cagggcggcg ttaagcttga acgaa                                  95

<210> SEQ ID NO 3
<211> LENGTH: 95
<212> TYPE: DNA
<213> ORGANISM: Artificial Sequence
<220> FEATURE:
<223> OTHER INFORMATION: Promoter 1

<400> SEQUENCE: 3
atgcgagtca aagcaagatc ggtgccggat cggcaccagt taggtcggaa aaaggcggca       60
gtcaagtgcg cagggcggcg ttataattga acgaa                                  95
```

<210> SEQ ID NO 4
<211> LENGTH: 82
<212> TYPE: DNA
<213> ORGANISM: Artificial Sequence
<220> FEATURE:
<223> OTHER INFORMATION: Promoter 2

<400> SEQUENCE: 4
tcggtgccgg atcggcacca gttaggtcgg aaaaaggcgg cagtcaagtg cgcttttttgt    60 acctataata gattcatgat ga                                              82

<210> SEQ ID NO 5
<211> LENGTH: 81
<212> TYPE: DNA
<213> ORGANISM: Artificial Sequence
<220> FEATURE:
<223> OTHER INFORMATION: Promoter 3

<400> SEQUENCE: 5
tcggtgccgg atcggcacca gttaggtcgg aaaaaggcgg cagtcaagtg cgcttttttgt    60 acctatatag attcatgatg a                                               81

<210> SEQ ID NO 6
<211> LENGTH: 81
<212> TYPE: DNA
<213> ORGANISM: Artificial Sequence
<220> FEATURE:
<223> OTHER INFORMATION: Promoter 4

<400> SEQUENCE: 6
tcggtgccgg atcggcacca gttaggtcgg aaaaaggcgg cagtcaagtg cgcttttttgt    60 acctataaag attcatgatg a                                               81

<210> SEQ ID NO 7
<211> LENGTH: 82
<212> TYPE: DNA
<213> ORGANISM: Artificial Sequence
<220> FEATURE:
<223> OTHER INFORMATION: Promoter 5

<400> SEQUENCE: 7
tcggtgccgg atcggcacca gttaggtcgg aaaaaggcgg cagacaagtg cgcttttttgt    60 acctataata gattcatgat ga                                              82

<210> SEQ ID NO 8
<211> LENGTH: 82
<212> TYPE: DNA
<213> ORGANISM: Artificial Sequence
<220> FEATURE:
<223> OTHER INFORMATION: Promoter 6

<400> SEQUENCE: 8
tcggtgccgg atcggcacca gttaggtcgg aaaaaggcgg cagacaagtg cgcttttttgt    60 acctataata gattcatgat ga                                              82

<210> SEQ ID NO 9
<211> LENGTH: 81
<212> TYPE: DNA
<213> ORGANISM: Artificial Sequence
<220> FEATURE:
<223> OTHER INFORMATION: Promoter 7

```
<400> SEQUENCE: 9
tcggtgccgg atcggcacca gttaggtcgg aaaaaggcgg cagacaagtg cgcttttttgt    60 acctatatag attcatgatg a                                               81

<210> SEQ ID NO 10
<211> LENGTH: 81
<212> TYPE: DNA
<213> ORGANISM: Artificial Sequence
<220> FEATURE:
<223> OTHER INFORMATION: Promoter 8

<400> SEQUENCE: 10
tcggtgccgg atcggcacca gttaggtcgg aaaaaggcgg cagacaagtg cgcttttttgt    60 acctataaag attcatgatg a                                               81

<210> SEQ ID NO 11
<211> LENGTH: 59
<212> TYPE: DNA
<213> ORGANISM: Artificial Sequence
<220> FEATURE:
<223> OTHER INFORMATION: Promoter 9

<400> SEQUENCE: 11
tcggtgccgg atcggcacct gacaggtcgg aaaaaggcgg ctataagtgc gcatgatga     59

<210> SEQ ID NO 12
<211> LENGTH: 42
<212> TYPE: DNA
<213> ORGANISM: Artificial Sequence
<220> FEATURE:
<223> OTHER INFORMATION: Promoter 10

<400> SEQUENCE: 12
ttgacaggtg ccggatcggc acctataata gattcatgat ga                        42

<210> SEQ ID NO 13
<211> LENGTH: 75
<212> TYPE: DNA
<213> ORGANISM: Artificial Sequence
<220> FEATURE:
<223> OTHER INFORMATION: Promoter 11

<400> SEQUENCE: 13
caagatcggt gccggatcgg caccagttag gtcttgacat cgcatctttt tgtacctata    60
atagattcat gatga                                                     75

<210> SEQ ID NO 14
<211> LENGTH: 46
<212> TYPE: DNA
<213> ORGANISM: Artificial Sequence
<220> FEATURE:
<223> OTHER INFORMATION: Promoter 12

<400> SEQUENCE: 14
ggtgccgaca cggcaccttt ttgtacctat aatagattca tgatga                    46

<210> SEQ ID NO 15
<211> LENGTH: 42
<212> TYPE: DNA
<213> ORGANISM: Artificial Sequence
<220> FEATURE:
<223> OTHER INFORMATION: Promoter 13

<400> SEQUENCE: 15
```
ttgacaggtg ccgatccggc acctataata gattcatgat ga                42

<210> SEQ ID NO 16
<211> LENGTH: 75
<212> TYPE: DNA
<213> ORGANISM: Artificial Sequence
<220> FEATURE:
<223> OTHER INFORMATION: Promoter 14

<400> SEQUENCE: 16
gacctaactg gtgccgatcc ggcaccgatc ttgttgacat cgcatctttt tgtacctata    60
atagattcat gatga                                                    75

<210> SEQ ID NO 17
<211> LENGTH: 59
<212> TYPE: DNA
<213> ORGANISM: Artificial Sequence
<220> FEATURE:
<223> OTHER INFORMATION: Promoter 15

<400> SEQUENCE: 17
ggtgccgatc cggcaccttg acatcgcatc tttttgtacc tataatagat tcatgatga    59

<210> SEQ ID NO 18
<211> LENGTH: 46
<212> TYPE: DNA
<213> ORGANISM: Artificial Sequence
<220> FEATURE:
<223> OTHER INFORMATION: Promoter 16

<400> SEQUENCE: 18
ggtgccgatc cggcaccttt ttgtacctat aatagattca tgatga                  46

<210> SEQ ID NO 19
<211> LENGTH: 42
<212> TYPE: DNA
<213> ORGANISM: Artificial Sequence
<220> FEATURE:
<223> OTHER INFORMATION: apFab71

<400> SEQUENCE: 19
ttgacatcgc atcttttgt acctataata gattcatgat ga                       42

<210> SEQ ID NO 20
<211> LENGTH: 24
<212> TYPE: DNA
<213> ORGANISM: Artificial Sequence
<220> FEATURE:
<223> OTHER INFORMATION: Bujard_RBS

<400> SEQUENCE: 20
gaattcatta aagaggagaa aggt                                          24

<210> SEQ ID NO 21
<211> LENGTH: 42
<212> TYPE: DNA
<213> ORGANISM: Artificial Sequence
<220> FEATURE:
<223> OTHER INFORMATION: apFab61

<400> SEQUENCE: 21
ttgacaatta atcatccggc tcgtttaata gattcattag ag                      42

<210> SEQ ID NO 22

```
<211> LENGTH: 22
<212> TYPE: DNA
<213> ORGANISM: Artificial Sequence
<220> FEATURE:
<223> OTHER INFORMATION: Bba_J61132

<400> SEQUENCE: 22
tctagagaaa gacaggatta ac                                              22

<210> SEQ ID NO 23
<211> LENGTH: 903
<212> TYPE: DNA
<213> ORGANISM: Artificial Sequence
<220> FEATURE:
<223> OTHER INFORMATION: DNA sequence optimized (for E. coli) AtzR

<400> SEQUENCE: 23
atgcaacacc tgcgtttcct gcactacatc gacgcggttg cgcgttgcgg tagcatccgt      60
gcggcggcgg agcaactgca tgttgcggcg agcgcggtga accgtcgtgt tcaagatctg     120
gagtacgaac tgggtacccc gatctttgag cgtctgccgc gtggtgtgcg tctgaccgcg     180
gcgggtgaac tgtttgttgc gtatgcgcgt cgtcgtaacg cggacctgga acaggtgcaa     240
agccagattc aagatctgag cggtatgaag cgtggccgtg ttaccctggc ggcgagccag     300
gcgctggcgc cggagttcct gccgcgtgtg atccacgcgt tcaggcgca acgtccgggt      360 attgcgttcg acgtgaaagt tctggatcgt gaacgtgcgg tgctggcggt taccgacttt     420
gcggcggatc tggcgctggt gtttaacccg ccggacctgc gtggcctgac cgttattgcg     480
caggcgcgtc aacgtatttg cgcggtggtt gcgagcgatc acccgctggc gaagcgtacc     540
agcctgcgtc tgaaagactg cctggattac ccgctggcgc tgccggacag cagcctgagc     600
ggtcgtaacg tgctggacga gctgtttgat aaaagcagcg cgcgtccgcg tccgcagctg     660
gttagcaaca gctatgagat gatgcgtggc ttcgcgcgtg aaaccggtgg cgtgagcttt     720
caaatcgaaa ttggtgcggg cagcaccgag ggtgaagttg cgatcccgat tgatgagcgt     780
agcctggcga gcggccgtgt ggttctggtt gcgctgcgtg aacgtgtgct gccggttgcg     840
agcgcggcgt ttgcggagtt cgttgcgggc aagctggcgg ataccaccca taatgcgacc     900
taa                                                                  903
```